(12) United States Patent
Sun et al.

(10) Patent No.: US 10,568,638 B2
(45) Date of Patent: Feb. 25, 2020

(54) INTELLIGENT ORTHOPEDIC SURGICAL SYSTEM

(71) Applicant: SHENZHEN FUTURTEC MEDICAL CO., LTD., Shenzhen, Guangdong Province (CN)

(72) Inventors: Donghui Sun, Shenzhen (CN); Xunjun Shi, Shenzhen (CN); Wei Huang, Shenzhen (CN); Xijie Liang, Shenzhen (CN)

(73) Assignee: SHENZHEN FUTURTEC MEDICAL CO., LTD., Shenzhen, Guangdong Province (CN)

( * ) Notice: Subject to any disclaimer, the term of this patent is extended or adjusted under 35 U.S.C. 154(b) by 174 days.

(21) Appl. No.: 15/559,037

(22) PCT Filed: Jun. 20, 2016

(86) PCT No.: PCT/CN2016/086375
§ 371 (c)(1),
(2) Date: Sep. 15, 2017

(87) PCT Pub. No.: WO2017/032156
PCT Pub. Date: Mar. 2, 2017

(65) Prior Publication Data
US 2018/0092648 A1 Apr. 5, 2018

(30) Foreign Application Priority Data
Aug. 24, 2015 (CN) .......................... 2015 1 0521623

(51) Int. Cl.
*A61B 17/00* (2006.01)
*A61B 17/16* (2006.01)
(Continued)

(52) U.S. Cl.
CPC .............. *A61B 17/16* (2013.01); *A61B 34/10* (2016.02); *A61B 34/20* (2016.02); *B25J 3/00* (2013.01);
(Continued)

(58) Field of Classification Search
CPC combination set(s) only.
See application file for complete search history.

(56) References Cited

U.S. PATENT DOCUMENTS

| 5,078,140 A | 1/1992 | Kwoh |
| 2013/0172903 A1 | 7/2013 | Suarez et al. |

(Continued)

FOREIGN PATENT DOCUMENTS

| CN | 104887312 A | 9/2015 |
| CN | 104997549 A | 10/2015 |

*Primary Examiner* — Sameh R Boles
(74) *Attorney, Agent, or Firm* — Cheng-Ju Chiang (57) ABSTRACT

An intelligent orthopedic surgical system comprises a switcher, a surgical location device, a surgical planning and monitoring device connected to the switcher, a C-arm X-ray apparatus and an orthopedic surgical robot. The orthopedic surgical robot comprises a robot body, a robot arm fixed to the robot body, an intelligent bone drill fixed to the robot arm, a communication module, a robot arm control module, an intelligent bone drill control module and a surgical robot electrical control module. The intelligent bone drill comprises a surgery electric drill, a guide mechanism for an electric drill head, a pushing mechanism, a visual identification system, a pressure sensor and a bone drill controller. The orthopedic surgical robot of the present system can perforate accurately under the navigation control and improve the accuracy and stability of the operation.

16 Claims, 6 Drawing Sheets (51) Int. Cl.
- *B25J 3/00* (2006.01)
- *B25J 11/00* (2006.01)
- *A61B 34/10* (2016.01)
- *A61B 34/20* (2016.01)
- *A61B 34/00* (2016.01)

(52) U.S. Cl.
CPC ............... *B25J 11/00* (2013.01); *A61B 34/25* (2016.02); *A61B 2034/101* (2016.02)

(56) References Cited

U.S. PATENT DOCUMENTS

| | | |
|---|---|---|
| 2014/0189508 A1 | 7/2014 | Granchi et al. |
| 2015/0100066 A1* | 4/2015 | Kostrzewski .......... A61B 34/30 606/130 |

\* cited by examiner

INTELLIGENT ORTHOPEDIC SURGICAL SYSTEM

CROSS REFERENCE TO RELATED APPLICATIONS

The present application is a 35 U.S.C. § 371 National Phase conversion of International (PCT) Patent Application No. PCT/CN2016/086375, filed on Jun. 20, 2016, which claims benefit of Chinese patent application No. 201510521623.8, filed on Aug. 24, 2015, the disclosure of which is incorporated by reference herein. The PCT International Patent Application was filed and published in Chinese.

FIELD OF THE INVENTION

The present invention relates to the field of medical appliances, and especially for an intelligent orthopedic surgical system.

BACKGROUND OF THE INVENTION

With the development of transportation industry, the occurrence of traffic accidents is also rising; trauma has become the leading cause of death worldwide. Orthopedic surgery has complicated types, although orthopedic surgical robot is available on the market, the existing orthopedic surgical robot at home and abroad can only perform auxiliary positioning functions of surgical instruments, and can not substitute the doctor to operate in practice. Although it can reduce the doctor's labor intensity, the surgical operation is still performed by the doctor, the accuracy of the operation still is easily deviated, and the labor intensity of the doctor is relatively heavy.

SUMMARY OF THE INVENTION

An object of the present invention is to provide an intelligent orthopedic surgical system, to solve the problem of the existing intelligent orthopedic surgical system with a robot can only perform auxiliary positioning function of surgical instruments.

An intelligent orthopedic surgical system is provided in accordance with the present invention. The intelligent orthopedic surgical system comprises a switcher, a surgical planning, a monitoring device, a C-arm X-ray apparatus, an orthopedic surgical robot, and a surgical location device connected with the switcher respectively. The orthopedic surgical robot comprises a robot body, a robot arm installed on the robot body, an intelligent bone drill fixed to the robot arm, a communication module, a robot-arm control module electrically connected with robot arm and the communication module respectively, an intelligent-bone-drill control module electrically connected with the intelligent bone drill and the communication module respectively, and an electrical control module of the surgical robot electrically connected with the intelligent-bone-drill control module and the robot-arm control module. The intelligent bone drill comprises a surgery electric drill, a guide mechanism connected at an electric drill head of the surgery electric drill, a pushing mechanism, a binocular visual system, a pressure sensor and a bone-drill controller installed on the surgery electric drill. The surgery electric drill, the guide mechanism, the binocular visual system and the pressure sensor are all mounted on the pushing mechanism. The bone-drill controller is electrically connected with the surgery electric drill, the pushing mechanism, the binocular visual system and the pressure sensor respectively.

The intelligent bone drill of the orthopedic surgical robot in accordance with the present invention comprises the binocular visual system, and the bone-drill controller is electrically connected with the binocular visual system. Therefore, not only the remote doctor can watch the real-time images of the surgical operation through the binocular visual system, but also the binocular visual system can provide the coordinate positioning before the surgical robot operates. In detail, a positioning method by the robot comprises: identifying the icons of the surgical location device on the patient body or surgical bed via the binocular visual system, establishing the 3D coordinates of the surgical location device, integrating a coordinate of the orthopedic surgical robot and a coordinate of the intelligent bone drill into the 3D coordinates determined by the surgical location device, and guiding the robot arm of the surgical robot to get to the corresponding coordinate position and posture state. Therefore, the orthopedic surgical robot in the present invention can accurately drill based on the navigation, and can perform operation, which thus can improve the accuracy and stability of the surgery, reduce the labor intensity of the doctor, and avoid disruptive factors to the surgery such as fatigue or psychological pressure etc.

DETAILED DESCRIPTION OF PREFERRED EMBODIMENTS

The objections, technology solutions and advantages of the present invention will be understood and appreciated more fully from the following detailed description taken in conjunction with the drawings. It should be understood that the embodiments described here only to explain the invention, not used to limit the invention.

The technology solutions of the present invention are described through the following detail embodiments.

Figure 1:
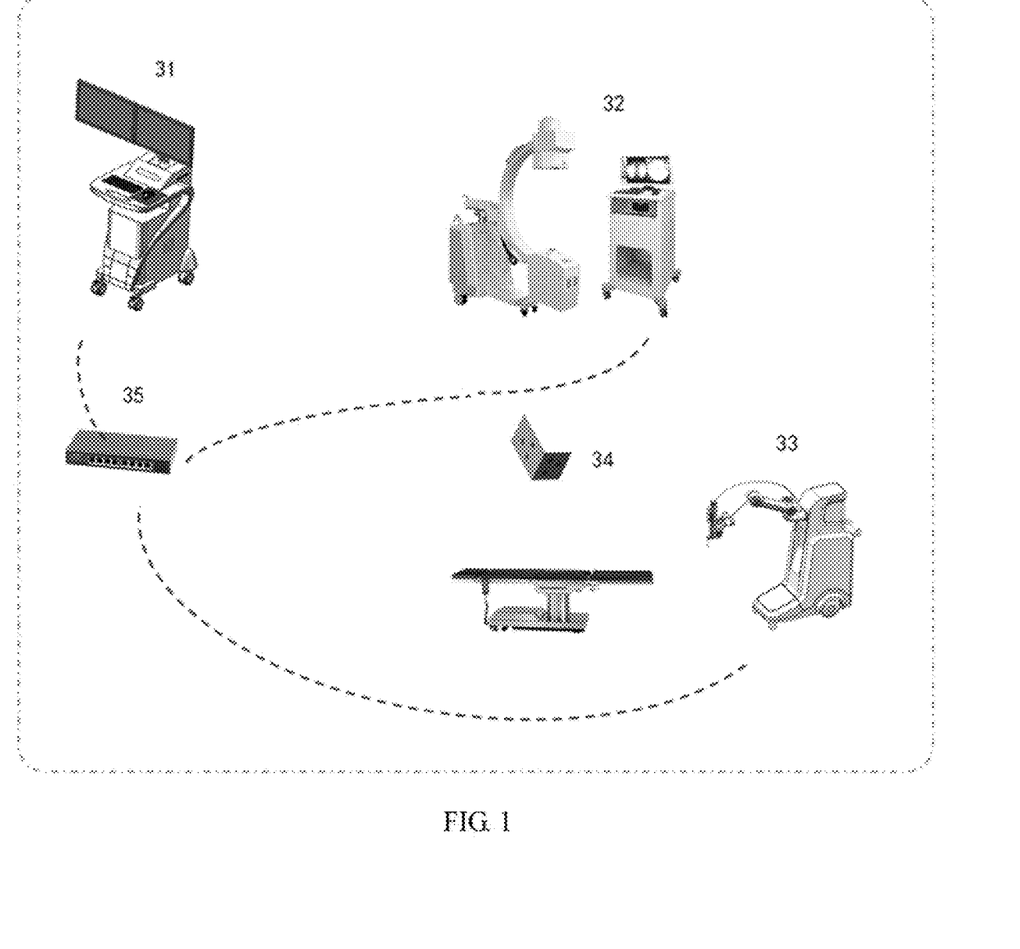
FIG. 1 is a schematic representation of an intelligent orthopedic surgical system in accordance with an embodiment of the present invention.

Referring to FIG. 1, an intelligent orthopedic surgical system provided in accordance with an embodiment of the present invention, comprises a surgical planning and monitoring device 31, a C-arm X-ray apparatus 32, an orthopedic surgical robot 33 and a surgical location device 34.

Wherein, the surgical planning and monitoring device 31: has a manually-movable operation table built in an image-workstation compute; the image-workstation computer is equipped with dedicated preoperative plan software and in-operation controlling software; the user can perform Graphics User Interface, 3D reconstruction of human bones, preoperative plan, surgical robot manipulation, and dynamic image monitoring in operation through the operation table.

The C-arm X-ray apparatus 32: is used to take X-ray images in vertical and horizontal orientations of the patient in operation, and transmits the X-ray images to the surgical planning and monitoring device 31 by a data line, matches multiple space coordinates through spatial variation algorithm, and accurately locates the surgical site of the patient.

The surgical planning and monitoring device 31, the C-arm X-ray apparatus 32, and the orthopedic surgical robot 33 are respectively connected with a switcher 35, thus data interaction and command execution between each device in the system can be performed. Herein, the switcher 35 can be an Ethernet switcher.

Figure 2:
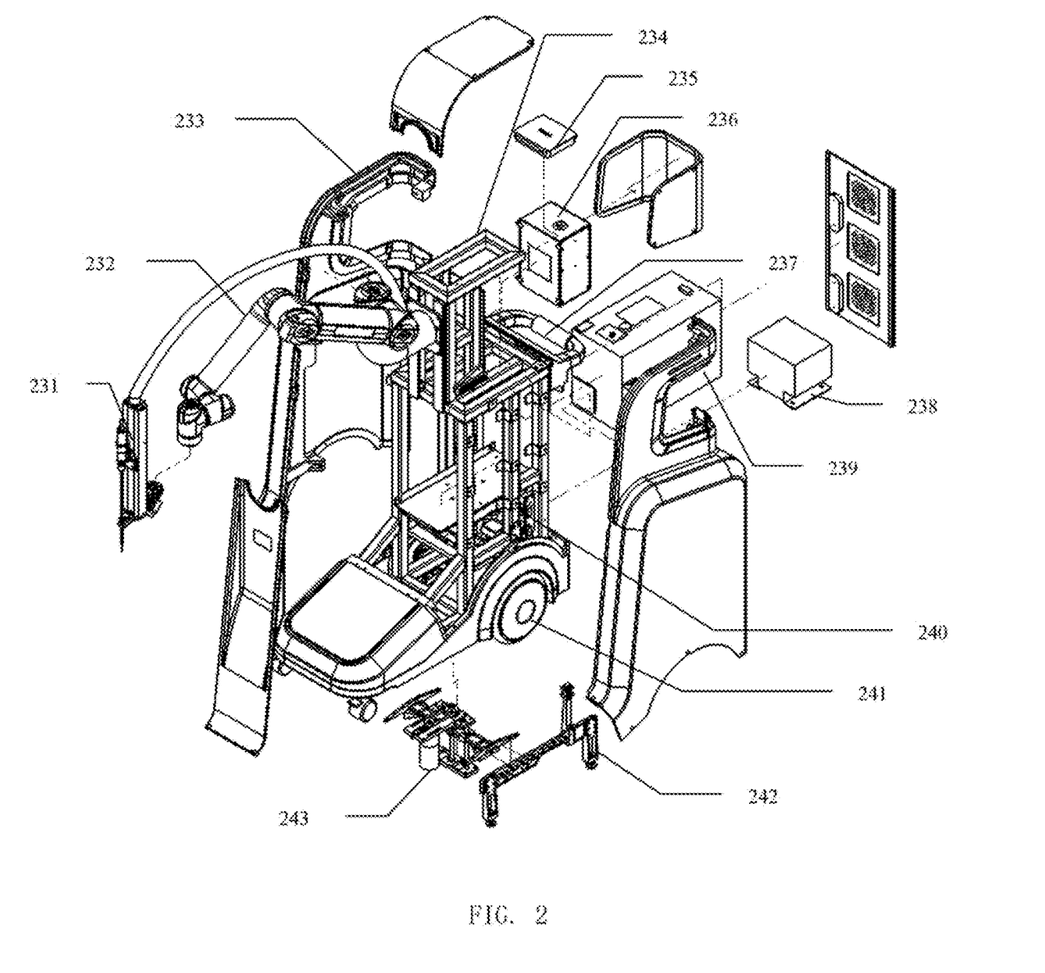
FIG. 2 is an exploded view of an orthopedic surgical robot in accordance with the embodiment of the present invention.
Figure 3:
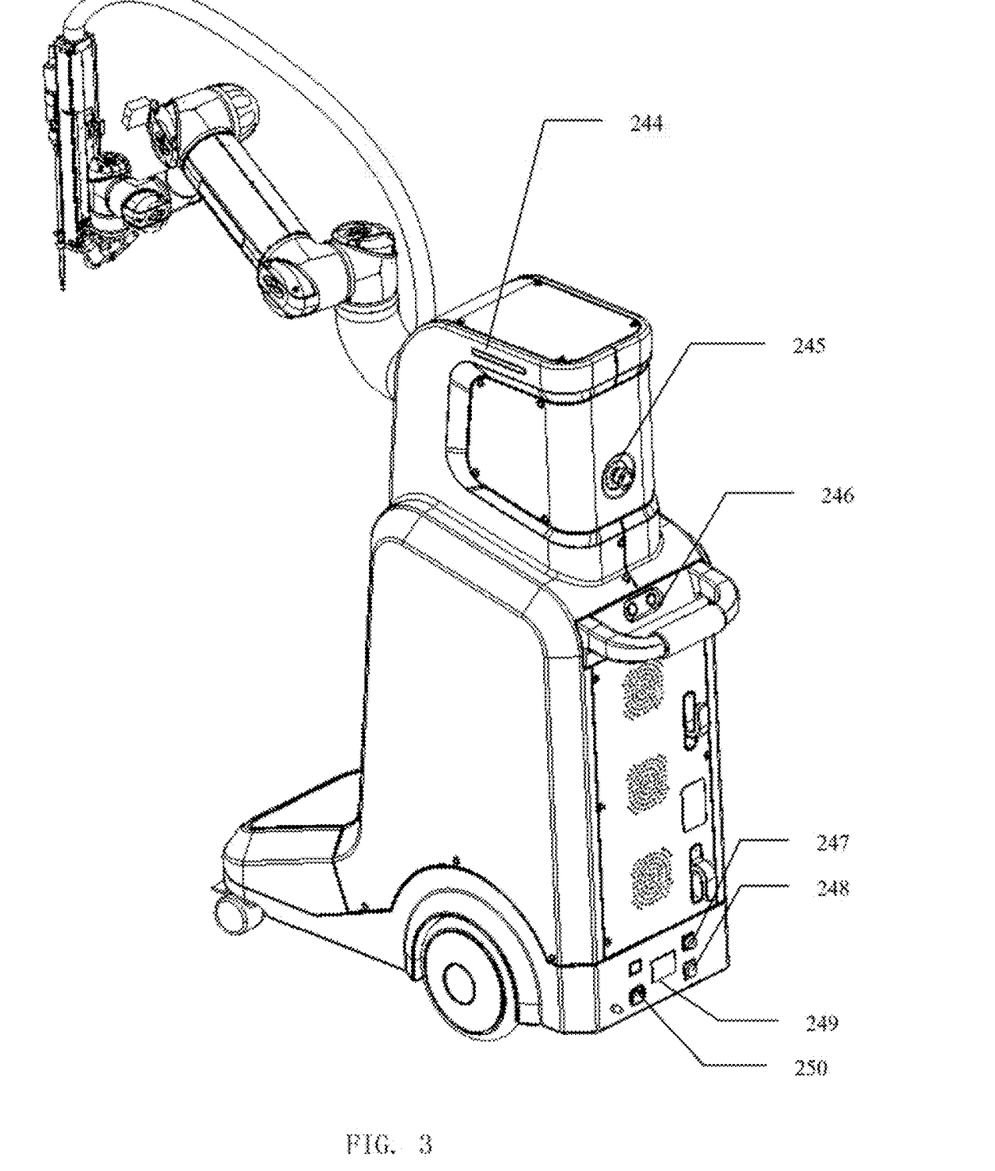
FIG. 3 is a perspective view of the orthopedic surgical robot in accordance with the embodiment of the present invention.

Referring to FIG. 2 and FIG. 3, the orthopedic surgical robot in accordance with the embodiment of the present invention comprises: a robot body 233, an robot arm 232 fixed on the robot body 233, an intelligent bone drill 231 fixed to the robot arm 232, a communication module 235, a robot-arm control module 239 electrically connected with the robot arm 232 and the communication module 235 respectively, an intelligent-bone-drill control module 236 electrically connected with the intelligent bone drill 231 and the communication module 235 respectively, and an electrical control module of the surgical robot electrically connected with the intelligent-bone-drill control module 236 and the robot-arm control module 239 respectively. The robot arm 232 can be six-axis robot arm.

The six-axis robot arm 232 is used to move the intelligent bone drill 231 to the desired surgical site, the intelligent bone drill 231 is used to perform the operation for the patient. The robot-arm control module 239 is used to control the six-axis robot arm 232. The intelligent-bone-drill control module 236 is used to control the intelligent bone drill 231. The communication module 235 can be an Ethernet switcher, and the Ethernet switcher is used to connect the intelligent-bone-drill control module 236 and the robot-arm control module 239 or the like together and then connect with an external network. The electrical control module of the surgical robot is used to provide an electrical control to the whole orthopedic surgical robot.

The six-axis robot arm 232 has six joint axes in total, the six joint axes are iii driven to rotate by six servomotors directly through a harmonic reducer and synchronous pulleys. Since the six-axis robot arm has six axis, and has six free parameters, its end can reach any desired position in any pose within an activity range of the joint.

The six joint axes of the six-axis robot arm 232 each has the same structure, and use two types of servomotors in different sizes, wherein, a spin axis (S axis), a lower-arm axis (L axis), and an upper-arm axis (U axis) use big servomotors; a wrist-rotating axis (R axis), a wrist-swing axis (B axis), and a wrist-revolving axis (T axis) use small servomotors. The joint axes simulate human arms in size and scale, so that the robot arm can reach any position in any pose within an available space range.

The six-axis robot arm 232 is mounted on a robot-arm seat of the robot body 233. A distal end of the robot-arm seat has a Flange, and the intelligent bone drill 231 is fixed on the six-axis robot arm 232 through the Flange. The intelligent bone drill 231 will perform operation after the six-axis robot arm 232 is positioned.

A left end and a right sides at the exterior periphery of the robot body 233 each has a three-color light sheet 244; the three-color light sheets 244 can emit light in a variety, different colors, and are respectively controlled by the robot-arm control module 239 and the intelligent-bone-drill control module 236, for indicating the operating states of both the six-axis robot arm and the orthopedic surgical robot.

The robot body 233 is equipped with four wheels 241 at a bottom thereof for easily moving. The robot body 233 is further equipped with electric foot brace 242 at the bottom thereof, the electric foot brace 242 can be driven to rise or fall by a DC motor through pulleys. The electric foot brace 242 is equipped with each limit switch 240 at top and bottom so as to limit the movement range of the electric foot brace 242. After the electric foot brace 242 falls, the robot body 233 is fixed on the floor; while the electric foot brace 242 rises, the robot body 233 can easily move through four wheels 241. A foot-brace motor 243 is controlled by two buttons 246 at a rear of the robot body 233 and close to a handle 237.

The robot body 233 at a lower rear thereof has power interface and control interface of the robot, and accordingly is equipped with a power input interface 250, a power switch 249 and a network interface 248 for external connection.

The electrical control module of the surgical robot comprises a power input socket, a power switch, a power filter, an isolation transformer 238, foot-brace buttons 246, a control circuit of foot-brace motor, an emergency-stop button 245 of the robot arm, an external emergency-stop button interface 247. Wherein, the isolation transformer 238 can isolate the whole power supply system of the orthopedic surgical robot from the municipal system, thus enhance the electric isolation between the interior of the orthopedic surgical robot and the municipal system, and improve the electricity safety of the orthopedic surgical robot. The isolation transformer is mounted at a bottom of a mounting frame for the orthopedic surgical robot.

The robot body 233 further comprises internal mounting frame 234. The mounting frame 234 is used to install other components of the surgical robot.

Figure 4:
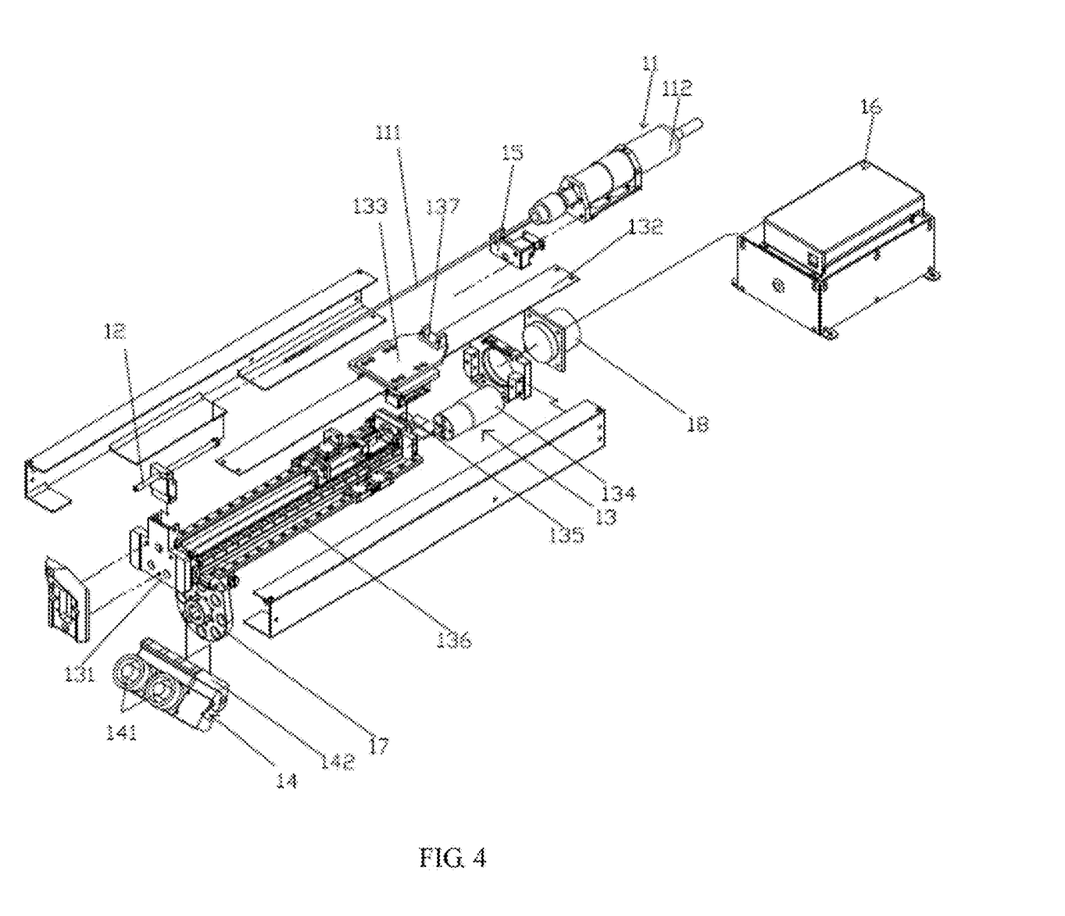
FIG. 4 is an exploded view of an intelligent bone drill in accordance with the embodiment of the present invention.
Figure 5:
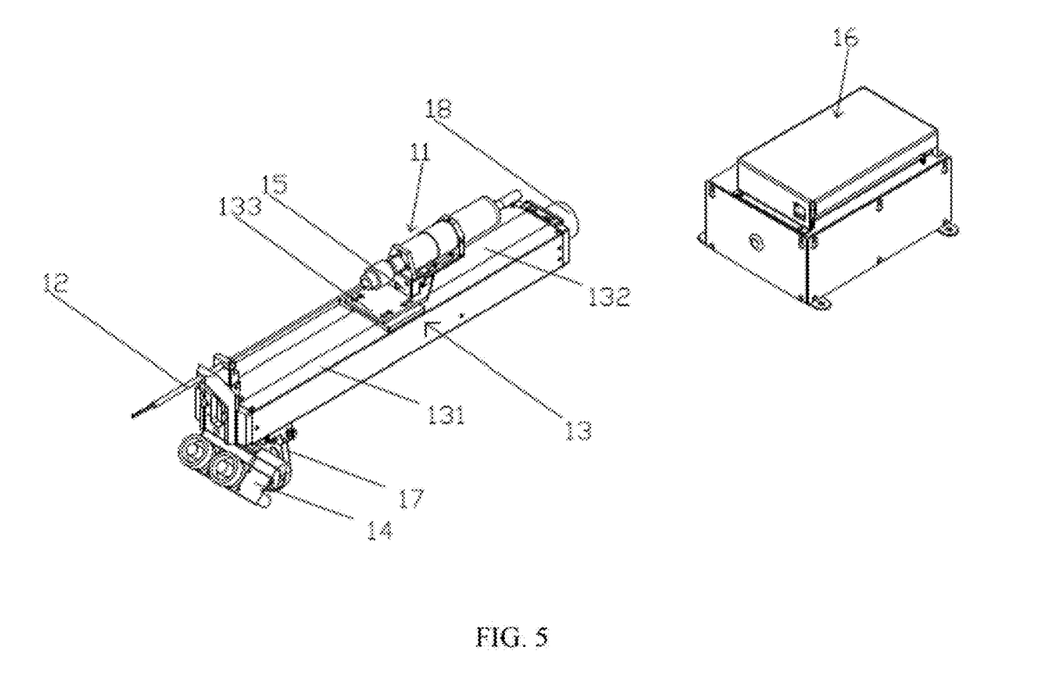
FIG. 5 is a perspective view of the intelligent bone drill in accordance with the embodiment of the present invention.

Referring to FIG. 4 and FIG. 5, the intelligent bone drill of the orthopedic surgical robot comprises a surgery electric drill 11, a guide mechanism 12 connected at an electric drill head 111 of the surgery electric drill 11, a pushing mechanism 13, a binocular visual system 14, a pressure sensor 15 and a bone-drill controller 16 fixed on the surgery electric drill 11. The surgery electric drill 11, guide mechanism 12, the binocular visual system 14 and the pressure sensor 15 are all mounted on the pushing mechanism 13; and the bone-drill controller 16 is electrically connected with the surgery electric drill 11, the pushing mechanism 13, the binocular visual system 14 and the pressure sensor 15 respectively.

The surgery electric drill 11 comprises an electric drill head 111 and a drill motor 112 driving the electric drill head 111 to perform the operation. The bone-drill controller 16 and the drill motor 112 of the surgery electric drill 11 are electrically connected.

The pushing mechanism 13 comprises a drill seat 131, a linear guide rail iii 132, a platform 133, a driving motor 134, a coupling 135 and ball screws 136. The linear guide rail 132 and the ball screws 136 are mounted on the drill seat 131; the platform 133 is mounted on the linear guide rail 132. The platform 133 is engaged with screw nuts of the ball screw 136 through a connection member. The driving motor 134 is mounted at a rear end of the drill seat 131; the platform 133 is coupled and driven by the driving motor 134 through the coupling 135 to linearly move back and forth. A fixing plate 137 of the surgery electric drill is mounted on the platform 133; and the surgery electric drill 11 is mounted on the fixing plate 137 through the pressure sensor 15. Thus, a force on the surgery electric drill 11 during the operation can be received by the pressure sensor 15. According to the force change in combination with a speed of the surgery electric drill 11, the tissue density and variation of the surgical site at the surgery electric drill 11 can be determined, and are compared to the parameters in the database of the system to confirm which tissue (skin, muscle, fat, periosteum, sclerotin, or bone marrow) of the human body the drill gets to, so as to avoid surgical accidents and provide surgical basis for the doctor.

The surgery electric drill 11 is controlled to propel or retreat by the driving motor 134. The driving motor 134 can be a brushless direct current speed reduction motor; the bone-drill controller 16 controls a rotation rate of the driving motor 134 by controlling the power frequency to the driving motor 134, in such way to control a speed of propelling or retreat of the surgery electric drill 11. A phase sequence of the power supply can control the surgery electric drill to propel or retreat. At the same time, through counting the rotation of the driving motor 134, a distance of the propelling or retreat can be measured.

The guide mechanism 12 is a sheath around the electric drill head 111 of the surgery electric drill 11 and mounted at a front end of the drill seat 131, is used to guide the electric drill head 111 to propel, isolates the electric drill head 111 from the muscle of the patient, and so as to protect the muscle around the surgical site moving with the rotation of the electric drill head 111.

The binocular visual system 14 comprises two cameras 141 and a fixing base 142 for fixing the two cameras 141; the two cameras 141 are mounted at a front lower part of the drill seat 131 through the fixing base 142 and photographing the electric drill head 111 and preferably photographing the guide mechanism 12. The two cameras 141 are arranged for a viewing angle besides the guide mechanism 12 around the tip of the electric drill head 111. The cameras 141 are connected to the surgical system with a network cable through the switcher 35. The operator and the authorised person can watch the real-time pictures of the two cameras 141 through network, and can directly watch three-dimensional images through a 3D imaging system. At the same time, the binocular visual system 14 can be further used for coordinate setting before the surgical robot operates. Because the intelligent bone drill 231 of the present invention has the binocular visual system 14, the remote doctor can watch real-time images of the surgical operation via the binocular visual system 14; further, the icons of the surgical location device 34 mounted on the patient or the surgical bed can be identified through the binocular visual system 14; thus three dimensional coordinates of the surgical location device 34 can be established, and the coordinates of both the orthopedic surgical robot 33 and the intelligent bone drill 231 can be integrated into the three dimensional coordinates established by the surgical location device 34. Thereby, the robot arm 232 of the surgical robot 33 can be guided to get to the corresponding coordinate and posture state.

The intelligent bone drill 231 is fixed to the six-axis robot arm 232 of the orthopedic surgical robot 33 through the flange 17, a drilling speed and depth can be accurately controlled according to the preoperative planning, a surgical deflection due to manual operation can be reduced, the accuracy of operation can be guaranteed, and the labor intensity of the doctor is reduced.

The intelligent bone drill 231 of the orthopedic surgical robot 33 in accordance with this embodiment of the present invention is controlled by the bone-drill controller 16 and software of PC, the bone-drill controller 16 is externally set to the intelligent bone drill 231, the bone-drill controller 16 is connected with the intelligent bone drill 231 through a control connector 18 at the drill seat 131. The bone-drill controller 16 is mainly used to control and measure the surgery electric drill 11 propelling, and measure the pressure sensor 15. Both the drill motor 112 and the driving motor 134 of the surgery electric drill 11 use brushless DC motor and has a built-in hall sensor each. The motor speed can be controlled by controlling frequency of the power supply to the motor, positive-negative rotation of the motor can be controlled by controlling the phase sequence of the power supply to the motor, and the motor speed can be measured by the Hall sensor. The bone-drill controller 16 is connected with PC through the network interface. It is very convenient for the PC to control the intelligent bone drill 231 using dedicated software, and to be connected with the binocular visual system through network.

Figure 6:
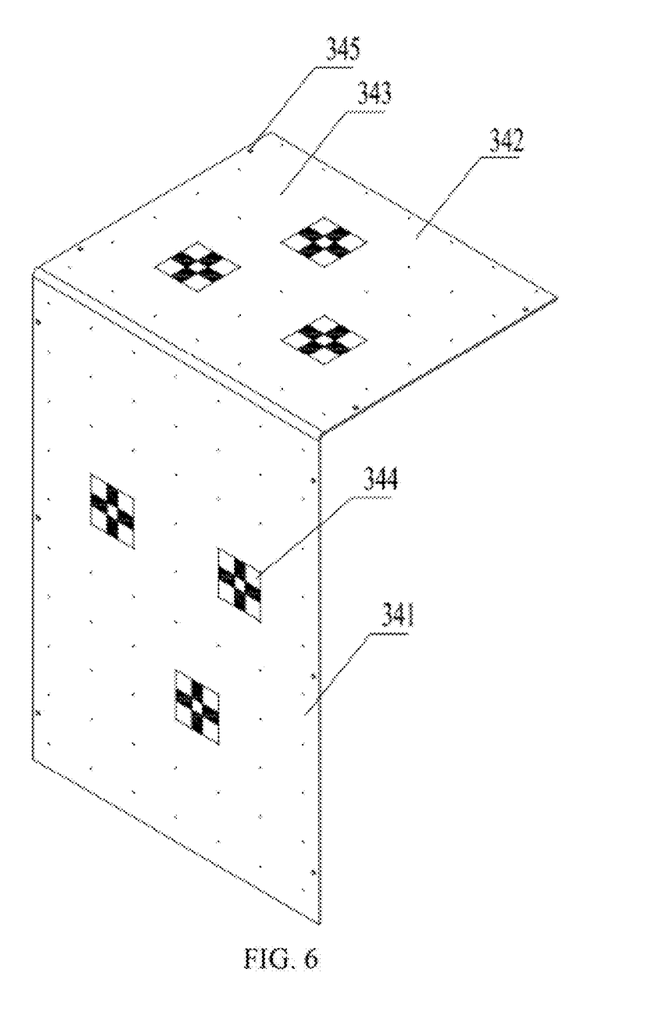
FIG. 6 is a schematic representation of a surgical location device in accordance with the embodiment of the present invention.

Referring to FIG. 6 together, the surgical location device 34 in accordance with the embodiment of the present invention, comprises a first positioning plate 341 and a second positioning plate 342 connected with each other. In accordance with one embodiment of the present invention, the first positioning and the second positioning plate 342 are vertical to each other, in such way to simplify calculation to establish the 3D-coordinate system. Of course, the first positioning plate 341 and the second positioning plate 342 may not be vertical to each other, namely, an angle between the first positioning plate 341 and the second positioning plate 342 is not 90 degree. The first positioning plate 341 and the second positioning plate 342 can be an integrated structure or connected with each other via a connecting member. Each of the first positioning plate 341 and the second positioning plate 342 has a base made from transparent plastic, and the base has been embedded with a plurality of metal pieces 343 based on location algorithm. The metal pieces 343 may be metallic balls, or metal blocks etc. The metal pieces 343 in the first positioning plate 341 and the second positioning plate 342 can be used for the X-ray apparatus to sense light in both horizontal and vertical directions, can block X-ray so as to form images on the X-ray film, and can be used for operation location.

Because the metal pieces 343 cannot be clearly identified in the binocular visual system 14 of the intelligent bone drill 231 in the surgical robot 33, therefore, there are at least three out-of-line icons 344 printed in the base of each the first positioning plate 341 and the second positioning plate 342 in the surgical location device 34 in accordance with the embodiment of this invention, for being identified by the binocular visual system 14. A plane can be determined via at least three icons 344 being out-of-line. Wherein, the binocular visual system 14 is constructed by two industrial cameras 141 mounted at a front lower part of the intelligent bone drill 231, the industrial cameras 141 are connected to the system with network cable through the Ethernet switcher 35, so that the operator and the authorised person can watch the real-time image of the two industrial cameras 141 through network; and the industrial cameras 141 are further used for coordinate location before the surgical robot operates.

The first positioning plate 341 and/or the second positioning plate 342 of the surgical location device 34 in accordance with the present invention, define mounting holes 345 in a rim thereof, for being mounted to a positioning bracket at the surgical bed or on the patient body.

In accordance with the embodiments of the present invention, the surgical location device 34 can be mounted in two way: one is to mount the positioning bracket at the surgical bed, and then to mount the surgical location device 34 on the positioning bracket; and the other is to mount the positioning bracket on the patient body, and then to mount the surgical location device on the positioning bracket.

The surgical location device 34 provided in the embodiment of the present invention can determine the 3D-coordinate system, because the surgical location device 34 comprises the metal pieces 343 and icons 344 being identified by the binocular visual system 14, the metal pieces 343 and icons 344 can be identified at the same time respectively by the X-ray apparatus 32 and the binocular visual system 14. Via the metal pieces 343 of the surgical location device 34, the X-ray apparatus 32 can position the surgical site into the 3D-coordinate system determined by the surgical location device 34. At the same time, via the icons 344, the binocular visual system 14 can calculate the position of the surgical robot 33 itself in the 3D-coordinate system determined by the surgical location device 34. Therefore, the coordinate of the surgical robot 33 and the coordinate of the intelligent bone drill 231 can be integrated into the 3D-coordinate system determined by the surgical location device 34. Therefore, the surgical robot 33 can be guided to get to the corresponding surgical site, which is more direct and accurate.

The orthopedic surgical robot of the existing intelligent orthopedic surgical system including the intelligent bone drill; however, the intelligent bone drill of the orthopedic surgical robot 33 in the present invention comprises the binocular visual system 14, the bone-drill controller 16 and the binocular visual system 14 are electrically connected. Therefore, the remote doctor can watch the real-time images of the surgical operation via the binocular visual system 14, and the binocular visual system 14 can be further used for the coordinate position before the surgical robot operates. In detail, a positioning method comprises by robot: identifying the icons of the surgical location device on the patient body or the surgical bed via the binocular visual system; establishing the 3D coordinates of the surgical location device; integrating the coordinate of the orthopedic surgical robot and the coordinate of the intelligent bone drill into the 3D coordinates determined by the surgical location device; and guiding the robot arm of the surgical robot to get to the corresponding coordinate position and posture state. Therefore, the orthopedic surgical robot in the present invention can accurately drill based on the navigation, and can perform operation, which thus can improve the accuracy and stability of the surgery, reduce the labor intensity of the doctor, and avoid disruptive factors to the surgery such as fatigue or psychological pressure etc.

A surgical process of the intelligent orthopedic surgical system in accordance with the embodiment of the present invention comprises: planning by human before operation; positioning by robot in operation, and intelligent monitoring in operation.

The orthopedic surgical robot can utilize computer to analyze and process images of the patient such as X-ray images, CT, and magnetic resonance imaging by overlaying; and then according to the analysis results, can control the robot arm to perform such operations or steps that the doctor cannot perform or cannot perform well enough as the robot; which can avoid ray hurting the doctor, reduce the labor intensity of the doctor, shorten time for operation, improve accuracy and quality of the operation, avoid the secondary reconstruction, and has good commonability.

In the present invention, the doctor sets the operation plan using his experience, and the orthopedic surgical robot performs the operation; such a human-machine intelligence operation method is revolutionary as for the history of the orthopedic operation. The accuracy of the orthopedic surgical robot combines the thoughts of the doctor, can enormously improve the level of the orthopedic surgery.

The skilled in the art can understood and implement that the whole or some steps of the method in above embodiments can be performed through programs instructing corresponding hardware, such programs can be stored in a computer readable storage medium, the storage medium is such as ROM/RAM, magnetic disks, optical disks etc.

The above description discloses the preferable embodiments of the present invention, not limits the scope of the invention, spirit of variations or modifications made to the equivalent, should be covered within the scope of the present invention.

What is claimed is:

1. An intelligent orthopedic surgical system comprising:
   a switcher;
   a surgical location device;
   a surgical planning and monitoring device, an X-ray apparatus with a C-arm, and an orthopedic surgical robot respectively connected with the switcher;
   wherein the orthopedic surgical robot further comprises:
      a robot body;
      a robot arm fixed on the robot body;
      an intelligent bone drill fixed to the robot arm;
      a communication module;
      a robot-arm control module electrically connected with the robot arm and the communication module respectively;
      an intelligent-bone-drill control module electrically connected with the intelligent bone drill and the communication module respectively; and
      an electrical control module of the surgical robot electrically connected with the intelligent-bone-drill control module and the robot-arm control module respectively;
   the intelligent bone drill comprises:
      a surgery electric drill;
      a guide mechanism connected at an electric drill head of the surgery electric drill;
      a pushing mechanism;
      a binocular visual system; and
      a pressure sensor and a bone-drill controller both fixed to the surgery electric drill;
   the surgery electric drill, the guide mechanism, the binocular visual system and the pressure sensor are mounted on the pushing mechanism; the bone-drill controller is electrically connected with the surgery electric drill, the pushing mechanism, the binocular visual system and the pressure sensor respectively.

2. The system of claim 1, wherein the surgery electric drill comprises the electric drill head and a drill motor to drive the electric drill head, and the bone-drill controller is electrically connected with the drill motor.

3. The system of claim 1, wherein the pushing mechanism comprises a drill seat, a linear guide rail, a platform, a driving motor, a coupling and ball screws; the linear guide rail and the ball screws are mounted on the drill seat, the platform is mounted on the linear guide rail, the platform is engaged with screw nuts of the ball screws through a connection member, the driving motor is mounted at a rear end of the drill seat, and the platform is coupled and driven by the driving motor through the coupling.

4. The system of claim 3, wherein the platform is equipped with a fixing plate for the surgery electric drill, the surgery electric drill is mounted on the fixing plate via the pressure sensor.

5. The system of claim 3, wherein the guide mechanism is a sheath sleeved around the electric drill head of the surgery electric drill and mounted at a front end of the drill seat.

6. The system of claim 3, wherein the binocular visual system comprises two cameras and a fixing base for fixing the cameras, the two cameras are mounted at a front lower part of the drill seat through the fixing base.

7. The system of claim 1, wherein the robot arm is a six-axis robot arm.

8. The system of claim 1, wherein the surgical location device comprises a first positioning plate and a second positioning plate connected with each other, each the first positioning plate and the second positioning plate has a base embedded with a plurality of metal pieces therein; there are at least three out-of-line icons printed at each of the first positioning plate and the second positioning plate; the surgical location device is mounted at a surgical bed or on a patient body.

9. The system of claim 8, wherein the base of each the first positioning plate and the second positioning plate is made from transparent plastic materials.

10. The system of claim 8, wherein the first positioning plate and the second positioning plate is an integrated structure or connected with each other using a connecting member.

11. An intelligent orthopedic surgical system, comprising:
a surgical location device;
a C-arm X-ray apparatus, and
an orthopedic surgical robot;
wherein the orthopedic surgical robot further comprises:
a robot body;
a robot arm fixed on the robot body;
an intelligent bone drill fixed to the robot arm;
a robot-arm control module electrically connected with the robot arm; and
an intelligent-bone-drill control module electrically connected with the intelligent bone drill;
the intelligent bone drill comprises:
a surgery electric drill;
a binocular visual system; and
a bone-drill controller;
the bone-drill controller is electrically connected with the surgery electric drill and the binocular visual system.

12. The system of claim 11, wherein the binocular visual system comprises two cameras and a fixing base for fixing the cameras, the two cameras are mounted at a front lower part of the intelligent bone drill through the fixing base and photographing the electric drill head.

13. The system of claim 11, wherein the surgical location device comprises a first positioning plate and a second positioning plate connected with each other, each the first positioning plate and the second positioning plate has a base embedded with a plurality of metal pieces therein; the surgical location device is mounted at a surgical bed or on a patient body.

14. The system of claim 13, wherein there are at least three out-of-line icons printed at each of the first positioning plate and the second positioning plate and identified by the binocular visual system.

15. The system of claim 14, wherein the binocular visual system identifies a coordinate of the surgical robot and a coordinate of the intelligent bone drill via the icons.

16. The system of claim 13, wherein the C-arm X-ray apparatus takes X-ray images in vertical and horizontal orientations of the patient and locates a surgical site of the patient via metal pieces in the surgical location device.

* * * * *